US010245057B2

(12) United States Patent
Brandt et al.

(10) Patent No.: US 10,245,057 B2
(45) Date of Patent: Apr. 2, 2019

(54) SURGICAL INSTRUMENTS INCLUDING KNIFE ASSEMBLIES WITH REDUCIBLE CUTTING HEIGHT

(71) Applicant: COVIDIEN LP, Mansfield, MA (US)

(72) Inventors: Kim V. Brandt, Loveland, CO (US); Allan G. Aquino, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 284 days.

(21) Appl. No.: 15/237,267

(22) Filed: Aug. 15, 2016

(65) Prior Publication Data
US 2017/0119415 A1 May 4, 2017

Related U.S. Application Data

(60) Provisional application No. 62/247,247, filed on Oct. 28, 2015.

(51) Int. Cl.
*A61B 17/285* (2006.01)
*A61B 17/28* (2006.01)
*A61B 18/14* (2006.01)
*A61B 34/30* (2016.01)

(52) U.S. Cl.
CPC .......... *A61B 17/285* (2013.01); *A61B 17/282* (2013.01); *A61B 17/2816* (2013.01); *A61B 18/1442* (2013.01); *A61B 34/30* (2016.02); *A61B 2018/146* (2013.01); *A61B 2018/1455* (2013.01)

(58) Field of Classification Search
CPC ................ A61B 17/285; A61B 17/295; A61B 2018/1452; A61B 2018/1455; A61B 2018/1457; A61B 2018/146; B25B 7/22
See application file for complete search history.

(56) References Cited

U.S. PATENT DOCUMENTS

| 5,445,638 | A | * | 8/1995 | Rydell | A61B 18/1482 606/171 |
|---|---|---|---|---|---|
| 5,797,941 | A | | 8/1998 | Schulze et al. | |
| 8,303,586 | B2 | | 11/2012 | Cunningham et al. | |
| 8,439,911 | B2 | * | 5/2013 | Mueller | A61B 17/295 606/51 |
| 8,444,664 | B2 | | 5/2013 | Balanev et al. | |
| 8,906,018 | B2 | * | 12/2014 | Rooks | A61B 17/28 606/52 |
| 8,968,309 | B2 | | 3/2015 | Roy et al. | |
| 9,017,370 | B2 | | 4/2015 | Reschke et al. | |
| 9,078,677 | B2 | | 7/2015 | Trees et al. | |
| 9,216,030 | B2 | * | 12/2015 | Fan | A61B 17/29 |
| 9,339,327 | B2 | | 5/2016 | Koss | |
| 9,526,518 | B2 | * | 12/2016 | Nobis | A61B 17/3201 |
| 9,572,621 | B2 | * | 2/2017 | Livneh | A61B 18/1442 |
| 9,585,714 | B2 | * | 3/2017 | Livneh | A61B 17/295 |
| 9,655,672 | B2 | * | 5/2017 | Artale | A61B 18/1442 |
| 9,782,216 | B2 | * | 10/2017 | Batchelor | A61B 17/285 |
| 9,788,848 | B2 | * | 10/2017 | Ward | A61B 17/29 |

(Continued)

Primary Examiner — Ryan J. Severson

(57) ABSTRACT

A knife assembly of a surgical end effector assembly includes a knife body defining a longitudinal axis and having first and second arms. The first arm has a first head including a cutting edge at a distal end thereof and the second arm has a second head. The first head is pivotable relative to the second head to reduce a cutting height during translation of the knife assembly through a knife channel defined within the end effector assembly.

15 Claims, 9 Drawing Sheets

(56) References Cited

U.S. PATENT DOCUMENTS

| | | | |
|---|---|---|---|
| 9,949,786 B2* | 4/2018 | Clauda | A61B 18/1445 |
| 2008/0015566 A1 | 1/2008 | Livneh | |
| 2009/0254081 A1 | 10/2009 | Allison et al. | |
| 2011/0054468 A1 | 3/2011 | Dycus | |
| 2012/0083786 A1 | 4/2012 | Artale et al. | |
| 2013/0255063 A1 | 10/2013 | Hart et al. | |
| 2014/0074084 A1* | 3/2014 | Engeberg | A61B 18/1206 606/33 |
| 2015/0105820 A1* | 4/2015 | Fan | A61B 17/29 606/206 |
| 2015/0105821 A1* | 4/2015 | Ward | A61B 17/29 606/206 |
| 2015/0209067 A1* | 7/2015 | Stamm | A61B 18/1442 606/174 |
| 2015/0272606 A1 | 10/2015 | Nobis | |
| 2016/0157924 A1 | 6/2016 | Ding et al. | |
| 2016/0206366 A1 | 7/2016 | Clauda et al. | |
| 2016/0278847 A1* | 9/2016 | Batchelor | A61B 17/285 |
| 2017/0119415 A1* | 5/2017 | Brandt | A61B 17/285 |
| 2017/0333064 A1* | 11/2017 | Ebner | A61B 17/0684 |
| 2017/0340379 A1* | 11/2017 | Batchelor | A61B 17/285 |

\* cited by examiner

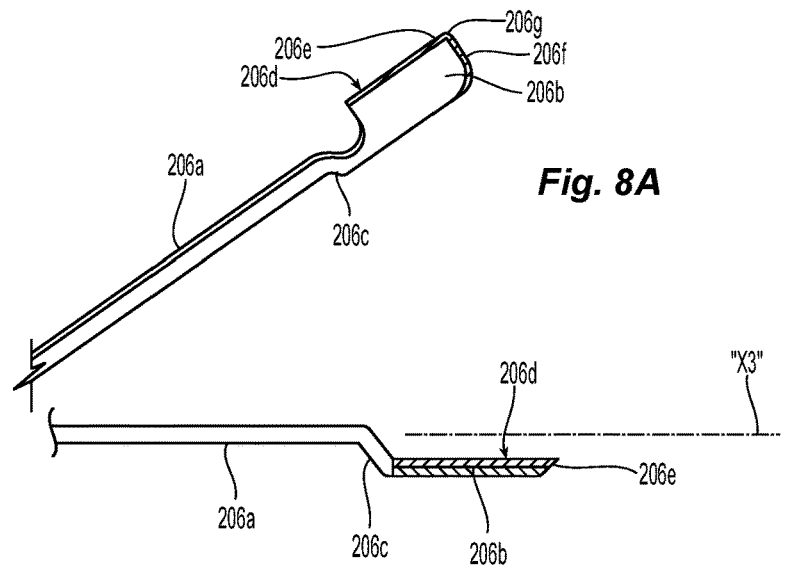
Fig. 8A
Fig. 8B
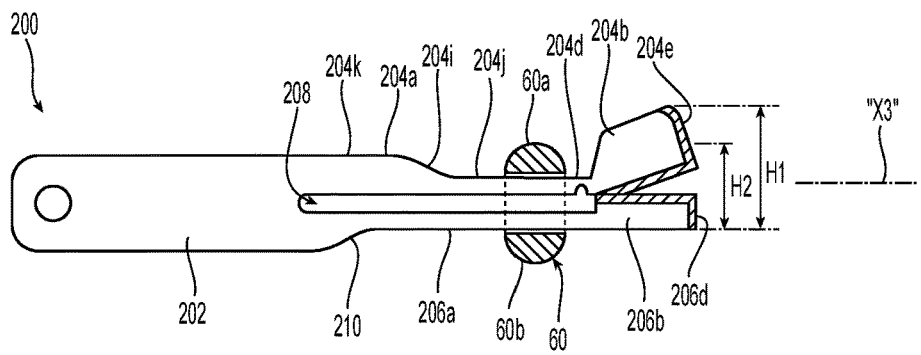
Fig. 9A
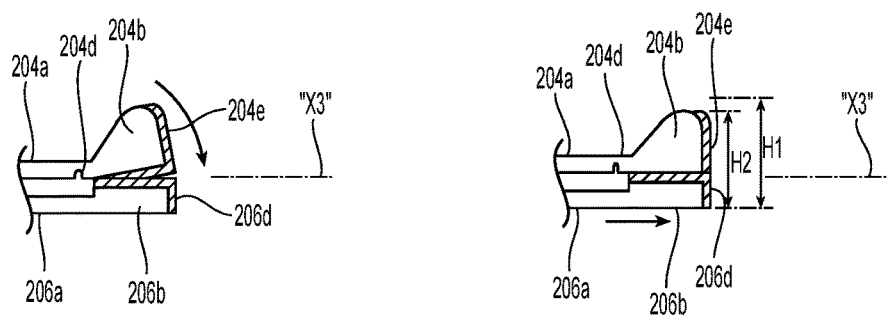
Fig. 9B  Fig. 9C

SURGICAL INSTRUMENTS INCLUDING KNIFE ASSEMBLIES WITH REDUCIBLE CUTTING HEIGHT

CROSS REFERENCE TO RELATED APPLICATION

The present application claims the benefit of and priority to U.S. Provisional Application Ser. No. 62/247,247, filed on Oct. 28, 2015, the entire contents of which are incorporated herein by reference.

TECHNICAL FIELD

The present disclosure relates to surgical instruments, and more particularly, to surgical instruments including knife assemblies with reducible cutting height for increasing blade travel through the surgical instruments.

BACKGROUND

Surgical instruments such as energy-based devices are typically used in conjunction with energy sources (external energy sources or portable energy sources incorporated into the instruments themselves) to apply and control the application of energy to tissue to thermally treat, e.g., heat, tissue to achieve a desired tissue effect. Electrosurgical forceps, for example, utilize both the mechanical clamping action of jaw members thereof and the energy provided by the energy source to heat tissue grasped between the jaw members for achieving a desired tissue effect, e.g., sealing tissue. Typically, after grasped tissue is sealed, a clinician advances a blade through the electrosurgical forceps to sever the sealed tissue while the sealed tissue is disposed between the jaw members.

Effective surgical instruments have blade configurations designed to guarantee complete tissue severance. Given that tissue may have many different shapes and dimensions, surgical instruments that account for such differences often provide superior effectiveness and/or usability. In performing finer dissection procedures, profiles of jaw members of surgical instruments are progressively becoming smaller, particularly at distal ends of the jaw members of these surgical instruments. Consequently, reduction of jaw member profiles increases the challenge of providing surgical instruments suitable for completely and efficiently severing the sealed tissue.

SUMMARY

Accordingly, one aspect of the present disclosure is directed to a knife assembly of a surgical end effector assembly. The knife assembly includes a knife body defining a longitudinal axis and having first and second arms. The first arm has a first head including a cutting edge at a distal end thereof and the second arm has a second head. At least the first head is pivotable relative to the second head to reduce a cutting height during translation of the knife assembly through a knife channel defined within the end effector assembly.

In certain embodiments, the first head may be coupled to the first arm by a first neck. The first neck may extend transverse to the longitudinal axis of the knife body.

In some embodiments, the first head includes a notch defined in a proximal end thereof. The notch may be configured to receive the second head therein. The first head may be configured to matingly receive the second head while the second head is received within the notch of the first head.

In certain embodiments, the first arm defines a first ramp configured to move the first arm relative to the second arm during translation of the knife assembly through the knife channel. The second arm may define a second ramp configured to move the second arm relative to the first arm during translation of the knife assembly through the knife channel. The first and second ramps may be longitudinally offset from one another.

In some embodiments, relative pivoting movement between the first and second heads causes the first and second heads to move between an unapproximated position and an approximated position. The first and second arms remain in the same plane while the first and second heads are in both the unapproximated and approximated positions. The first head may be pivotally coupled to the first arm by a living hinge.

In certain embodiments, the first head defines a first head ramp configured to move the first head relative to the first arm and the second head defines a second head ramp configured to move the second head relative to the second arm. The first and second heads may be pivotable during translation of the knife assembly through the knife channel. The first and second head ramps may be longitudinally offset.

In some embodiments, the second head includes a cutting edge. The cutting edges of the first and second heads may be positioned to create a scissor-cutting action between the cutting edges thereof as at least the first head pivots relative to the second head. The cutting edge of the first head may include a first longitudinal cutting edge and a first transverse cutting edge. The cutting edge of the second head may include a second longitudinal cutting edge and a second transverse edge. The first and second longitudinal cutting edges may be configured to cut in a shear direction transverse to the longitudinal axis of the knife body. The first and second transverse cutting edges may be configured to cut in an axial direction along the longitudinal axis of the knife body.

In certain embodiments, the first longitudinal cutting edge may be joined with the first transverse cutting edge by a first corner and the second longitudinal cutting edge may be joined to the second transverse cutting edge by a second corner. The first and second corners may be configured to cut in both the shear and axial directions relative to the longitudinal axis of the knife body.

In another aspect of the present disclosure, an end effector assembly is provided. The end effector assembly includes a pair of jaw members and a knife assembly. The pair of jaw members defines a knife channel between the pair of jaw members. The knife channel extends longitudinally along the pair of jaw members. The knife assembly defines a longitudinal axis and is positionable within the knife channel of the pair of jaw members.

In some embodiments, one or both of the pair of jaw members may taper from a distal portion of the pair of jaw members to a distal tip. The knife channel of the pair of jaw members may extend distally beyond the distal portion of the pair of jaw members to a distal end portion of the knife channel. The cutting edge of the first head may be receivable within the distal end portion of the knife channel.

In certain embodiments, the end effector assembly further includes a bifurcated pivot boss. The pair of jaw members may be configured to pivot about the bifurcated pivot boss. The knife assembly may be receivable through the bifurcated pivot boss. The bifurcated pivot boss may include one or more contact surfaces. The one or more contact surfaces are configured to contact one or more ramps of the knife assembly. Contact between the one or more contact surfaces of the bifurcated pivot boss and the one or more ramps of the knife assembly may reduce the height of the first head from a proximal height to a distal height. The one or more ramps may be supported on the first arm, the second arm, the first head, the second head, or combinations thereof.

In certain embodiments, the second head is pivotally coupled to the second arm.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description given below, serve to explain the principles of the disclosure, wherein:

FIGS. 8A and 8B are perspective and top views of a second portion of the knife assembly of FIG. 6;

FIGS. 9A-9C are progressive side views illustrating advancement of the knife assembly of FIG. 6 through the jaws members of FIGS. 3A and 3B;

DETAILED DESCRIPTION

Figure 1:
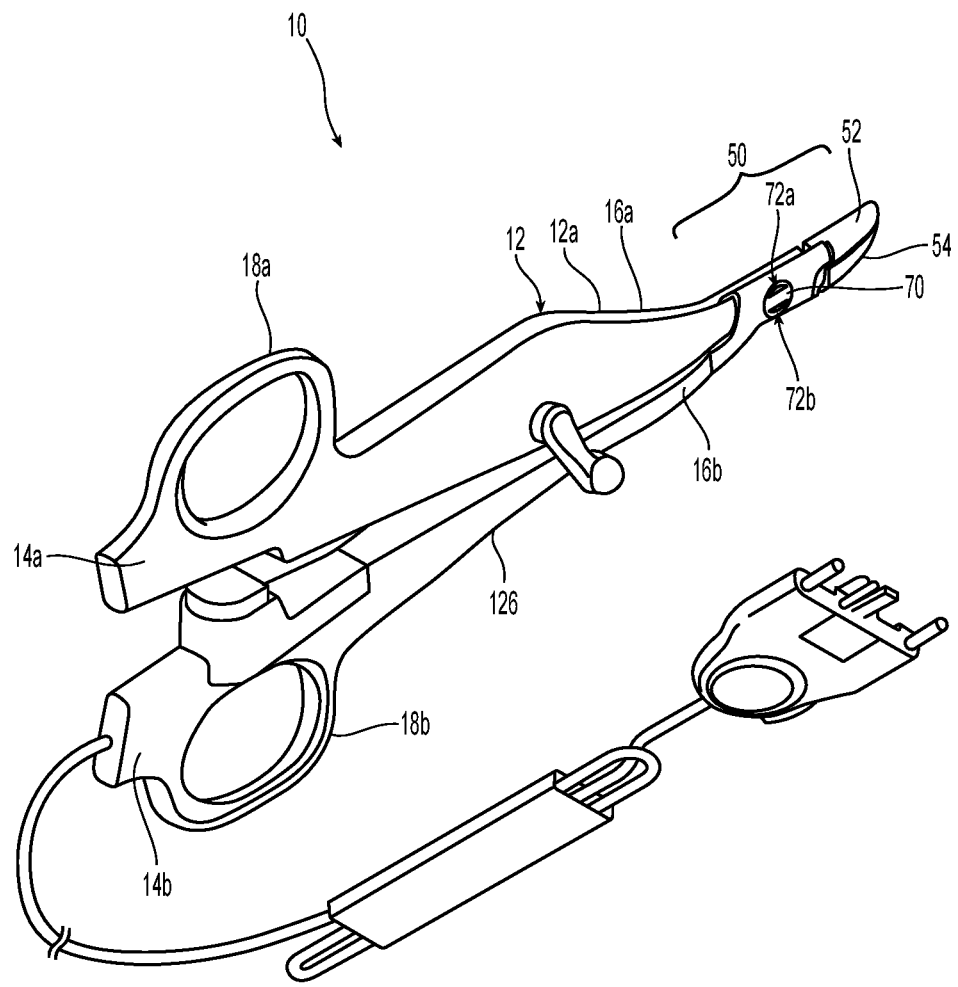
FIG. 1 is a perspective view of a surgical instrument in accordance with the principles of the present disclosure.

Particular embodiments of the present disclosure are described hereinbelow with reference to the accompanying drawings in which like reference numerals designate identical or corresponding elements in each of the several views. As used herein, the term "distal" refers to that portion of the system, device, and/or component(s) thereof, which is farther from the user, while the term "proximal" refers to that portion of the system, device, and/or component(s) thereof, which is closer to the user. In the following description, well-known functions or constructions are not described in detail to avoid obscuring the present disclosure in unnecessary detail.

Surgical systems in accordance with the present disclosure can include endoscopic and/or open surgical instruments such as forceps devices, ultrasonic dissection devices, and/or any other suitable surgical devices. Obviously, different electrical and mechanical connections and considerations apply to each particular type of device; however, the aspects and features of the present disclosure remain generally consistent regardless of the particular device used. For a detailed description of the construction and operation of exemplary surgical devices, reference may be made to U.S. Patent Application Publication No. 2013/0255063, filed on Mar. 29, 2012 and/or U.S. Pat. No. 8,444,664, filed on May 16, 2011, the entirety of each of which is incorporated by reference herein.

In the interest of brevity, surgical systems of the present disclosure will only be described herein in connection with an open surgical forceps.

Figure 2:
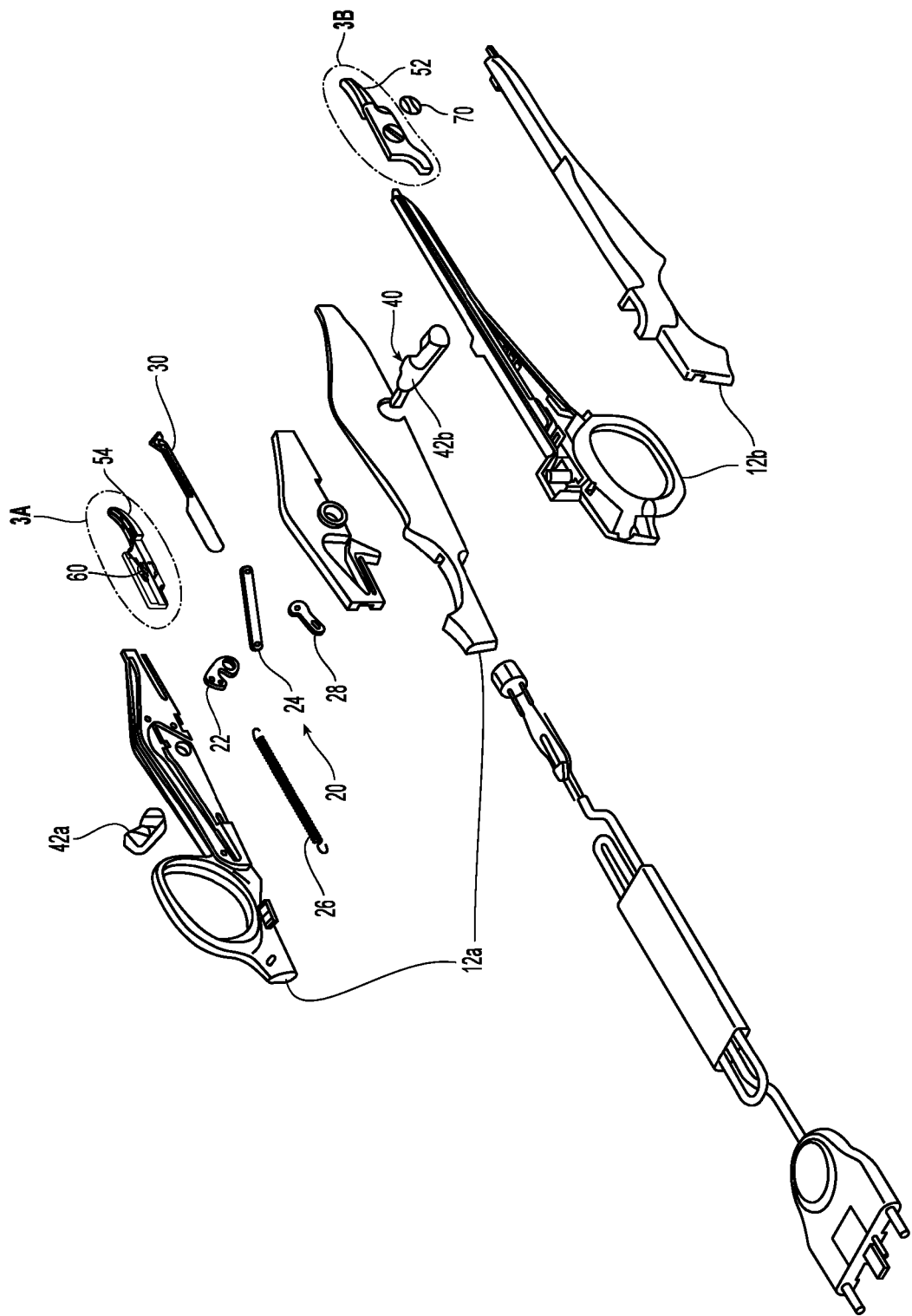
FIG. 2 is a perspective view, with parts separated, of the surgical instrument of FIG. 1.

Referring initially to FIGS. 1 and 2, a forceps 10 for use with open surgical procedures generally includes a shaft assembly 12 having elongated shafts 12a, 12b. The elongated shafts 12a, 12b have proximal 14a, 14b and distal ends 16a, 16b, respectively. The shafts 12a, 12b include handles 18a, 18b disposed at the proximal ends 14a, 14b thereof, respectively.

The shaft assembly 12 supports an actuating mechanism 20 and a knife assembly 30. The actuating mechanism 20 includes a trigger link 22, a knife pushing link 24, a spring 26, and an anti-deployment link 28. The actuating mechanism 20 is also operatively associated with a trigger assembly 40 having trigger handles 42a, 42b disposed on opposing sides of the shaft assembly 12 to facilitate left-handed and right-handed operation of the trigger assembly 40. The trigger assembly 40 is operatively associated with the actuating mechanism 20 so that the actuating mechanism 20 and the trigger assembly 40 mechanically cooperate to actuate the knife assembly 30.

Figure 3A:
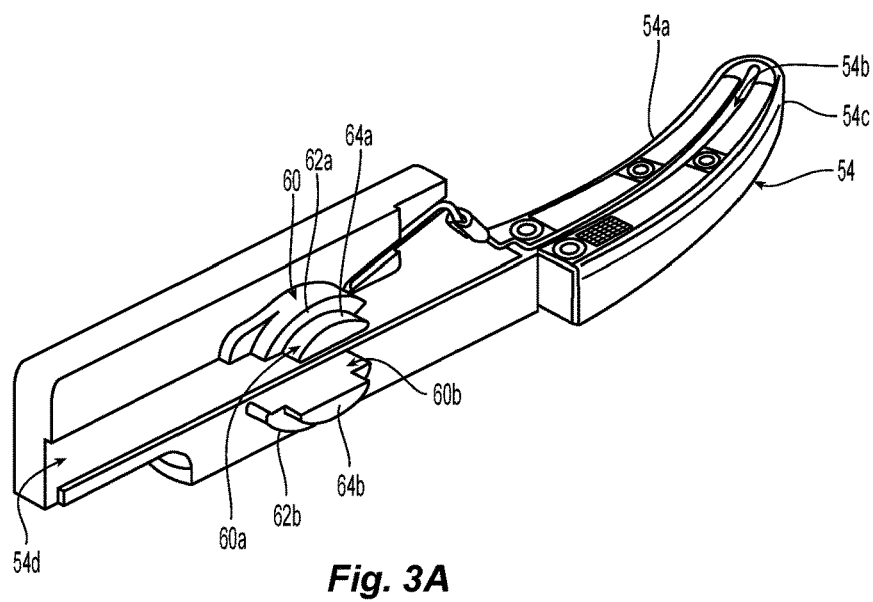
FIGS. 3A and 3B are enlarged, perspective views of one embodiment of jaw members of the surgical instrument shown in FIGS. 1 and 2.
Figure 3B:
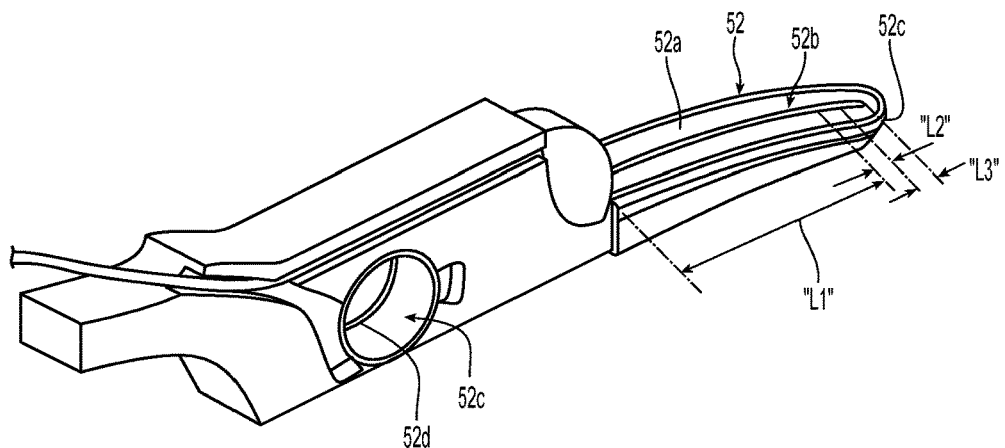
Figure 3C:
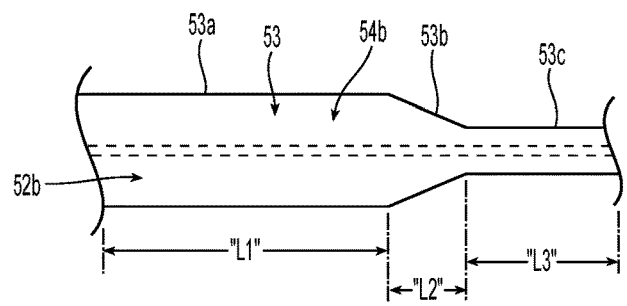
FIG. 3C is a schematic illustration of a knife channel defined between the jaw members of FIGS. 3A and 3B.

Referring also to FIGS. 3A-3C, the forceps 10 further includes an end effector assembly 50 attached to the distal ends 16a, 16b of the shafts 12a, 12b, respectively. The end effector assembly 50 includes a pair of opposing jaw members 52, 54 having tissue grasping portions 52a, 54a. The tissue grasping portions 52a, 54a of the jaw members 52, 54 define knife slots 52b, 54b, respectively, configured to enable reciprocation of the knife assembly 30 therethrough. The knife slots 52b, 54b together define a knife channel 53 having any number of portions such as a first portion 53a, a second portion 53b, and a third portion 53c, one or more of which may define a length and/or a height different than (or the same as) one or more of the other portions of the first, second, and third portions 53a-53c. For example, first portion 53a may define a first length "L1," the second portion 53b may define a second length "L2," and the third portion 53c may define a third length "L3." In some embodiments, one or more of the first, second, and third portions 53a-53c of the knife channel 53 may have multiple heights (e.g., a tapered configuration), for example, to transition from one of the first, second, and third portions 53a-53c to another of the other of the first, second, and third portions 53a-53c. The heights along one or more of these portions 53a-53c of the knife channel 53 can be configured to enable the knife assembly 30 to cut at a range of cutting heights, for example, larger dissection to smaller dissection (e.g., fine) heights.

The jaw members 52, 54 further include tapered or smaller tips 52c, 54c, respectively that are configured to effectuate finer tissue dissection therewith. In some embodiments, one or both of the second and third portions 53b, 53c of the knife channels 52b, 54b extend (e.g., from the first portion 53a) along the tips 52c, 54c of the first and second jaw members 52, 54 to elongate the knife channels 54b, 54c for providing finer tissue dissections as compared to through the first portion 53a of the knife channels 54b, 54c. In certain embodiments, one or both of at least portions of the jaw members 52, 54 may be tapered from a proximal end to a distal end of the jaw members 52, 54.

The jaw members 52, 54 are movable relative to one another about a pivot or bifurcated pivot boss 60 between open and closed positions to selectively grasp tissue. The bifurcated pivot boss 60 is disposed on a proximal end of the jaw member 54 and includes first and second opposing halves 60a, 60b disposed on opposing sides of a through channel 54d defined by the jaw member 54. As seen in FIG. 3A, the first and second opposing halves 60a, 60b of the bifurcated pivot boss 60 are disposed on opposing sides of the through channel 54d of the jaw member 54 to facilitate translation of the knife assembly 30 through the through channel 54d and the bifurcated pivot boss 60. The first and second opposing halves 60a, 60b are disposed in a split spherical configuration and include base portions 62a, 62b, respectively, that support extension portions 64a and 64b thereon, respectively.

The bifurcated pivot boss 60 connects through an aperture 52c defined through the jaw member 52. The bifurcated pivot boss 60 matingly engages a pivot plate 70 (FIG. 1) seated within a circumferential lip or flange 52d (FIG. 3B) defined around a periphery of the aperture 52c of jaw member 52 such that the bifurcated pivot boss 60 is rotatably movable within the aperture 52c to move the jaw members 52 and 54 between open and closed positions. The extension portions 64a, 64b of the first and second opposing halves 60a, 60b are receivable within complementary apertures 72a, 72b (FIG. 1) defined through the pivot plate 70 to pivotably secure the jaw members 52, 54 together.

For a more detailed description of the construction and operation of similar forceps or components thereof, reference may be made to U.S. Patent Application Publication No. 2012/0083786, filed on Oct. 4, 2010, the entire contents of which are incorporated by referenced herein.

Figure 4A:
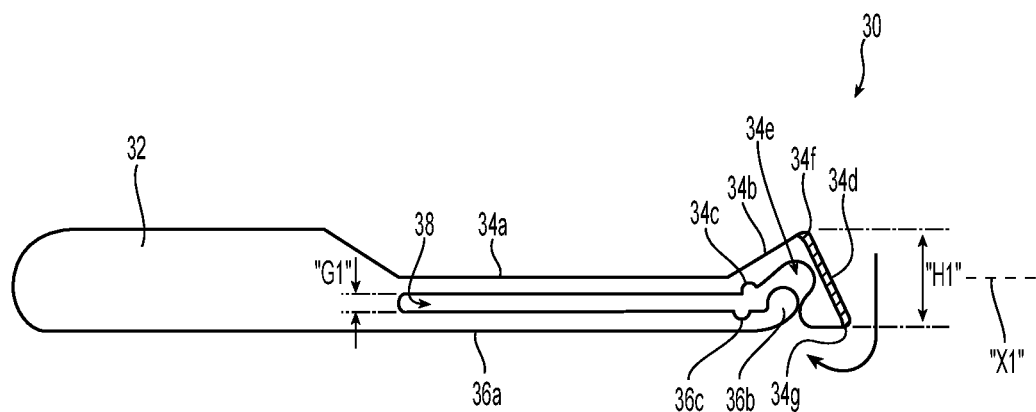
FIGS. 4A and 4B are progressive side views illustrating advancement of one embodiment of a knife assembly through the jaws members of FIGS. 3A and 3B.
Figure 4B:
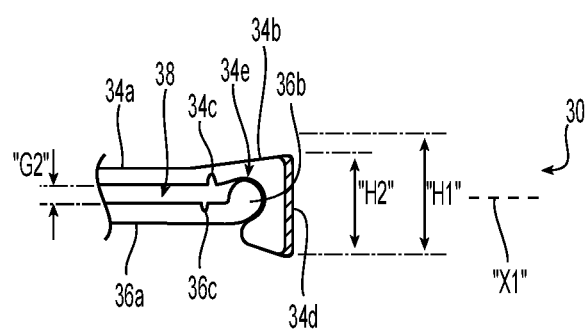
Figure 5A:
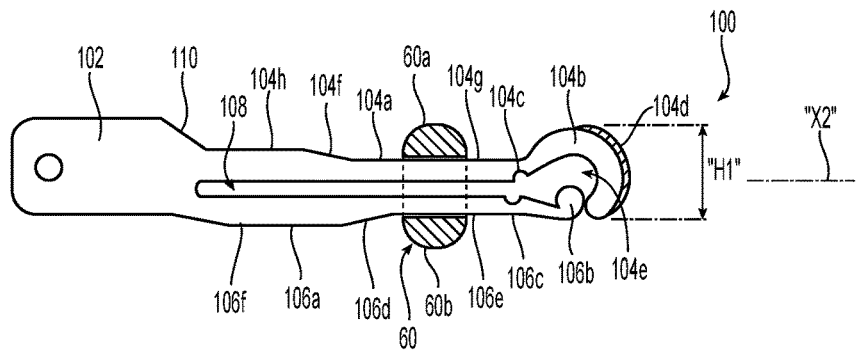
FIGS. 5A-5D are progressive side views illustrating advancement of another embodiment of a knife assembly through the jaws members of FIGS. 3A and 3B.
Figure 5B:
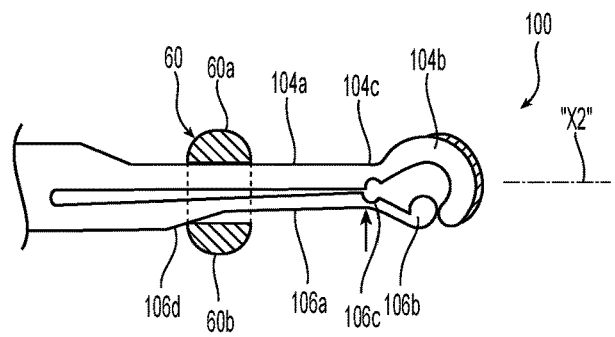
Figure 5C:
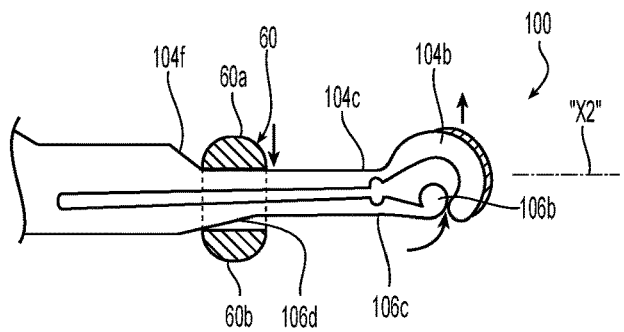
Figure 5D:
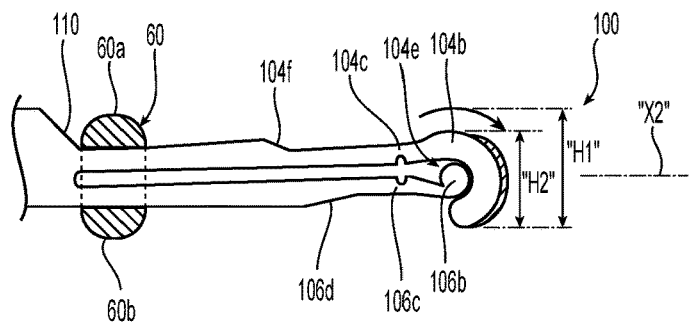
Figure 6:
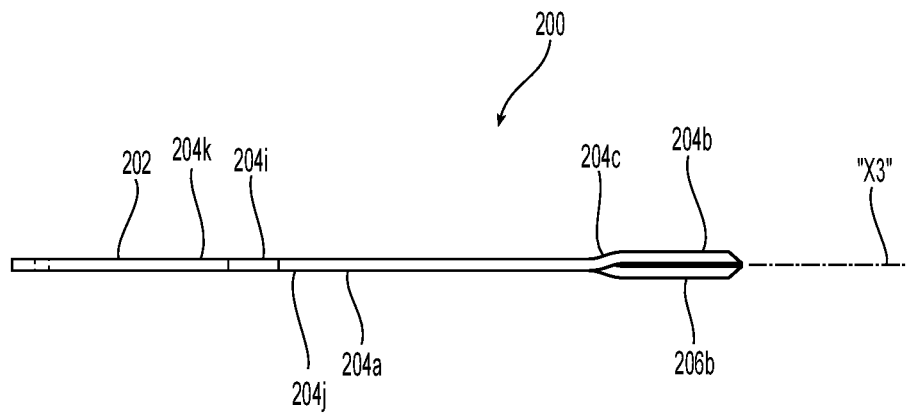
FIG. 6 is a top view of still another embodiment of a knife assembly.
Figure 7B:
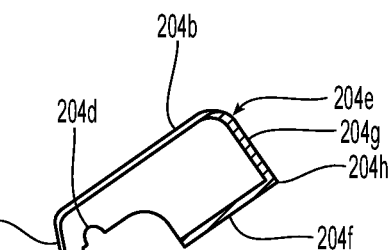
FIGS. 7A and 7B are perspective and top views of a first portion of the knife assembly of FIG. 6.
Figure 7A:
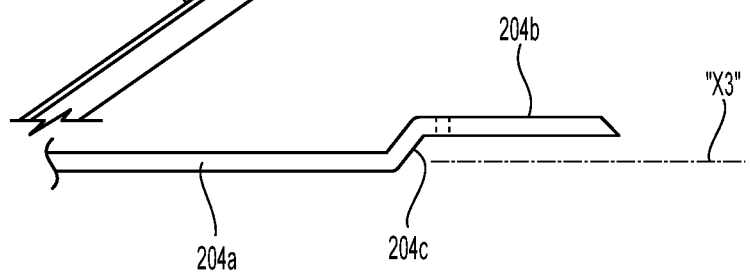
Figure 10A:
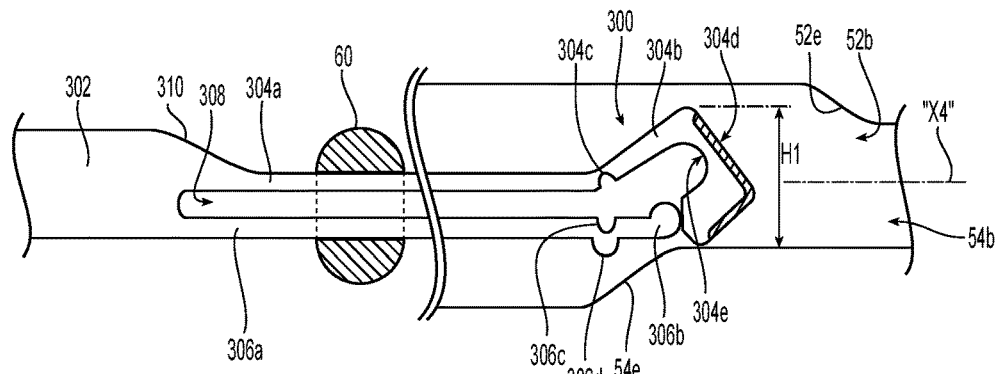
FIGS. 10A-10D are progressive side views illustrating advancement of yet another embodiment a knife assembly through another of embodiment of the jaw members of FIGS. 3A and 3B.
Figure 10B:
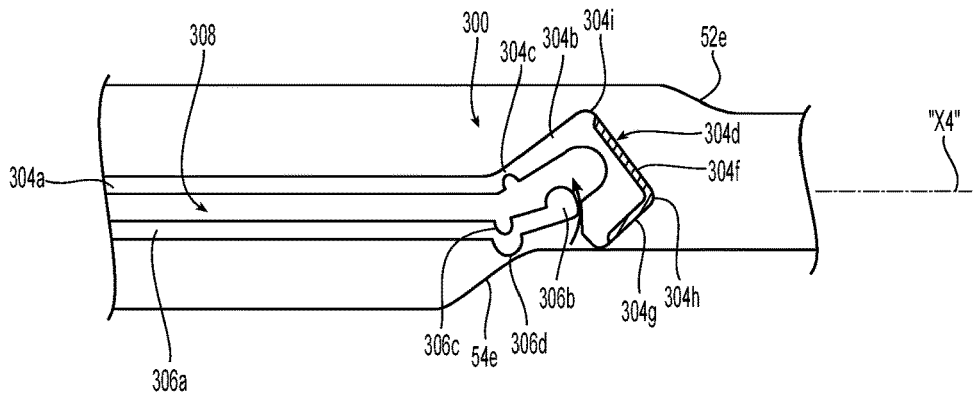
Figure 10C:
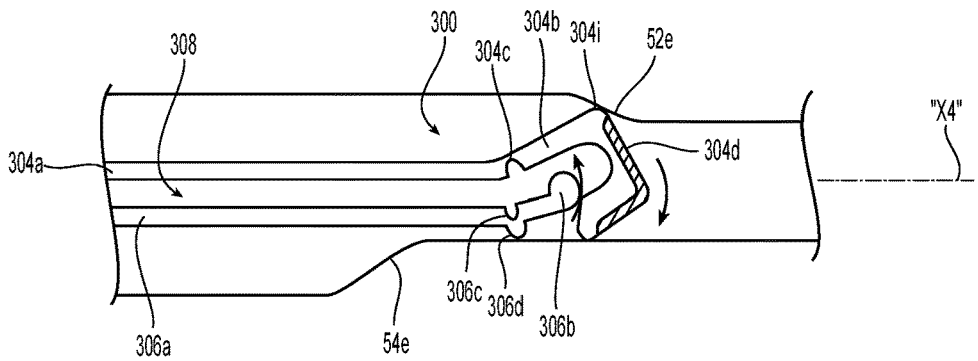
Figure 10D:
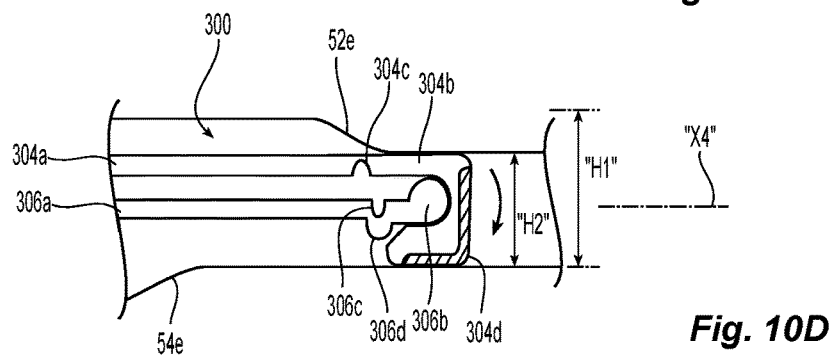

Turning now to FIGS. 4A and 4B, the knife assembly 30 defines a longitudinal axis "X1" and includes a knife body 32 having a first arm 34a and a second arm 36a. The first and second arms 34a, 36a extend distally from the knife body 32 and are spaced apart by a gap 38 defined between inner surfaces of the first and second arms 34a, 36a. The first and second arms 34a, 36a are disposed in vertical registration with one another.

The first arm 34a of the knife assembly 30 extends distally to a first head 34b pivotally coupled to the first arm 34a by a living hinge 34c. A distal surface of the first head 34b includes a cutting edge or knife blade 34d and a proximal surface of the first head 34b defines a notch 34e therein. The first head 34b further includes one or more engagement surfaces 34f and/or 34g.

The second arm 36a of the knife assembly 30 extends distally to a second head 36b selectively receivable within the notch 34e of the first head 34b. The second head 36b may have any suitable configuration such as rounded or blunt. The second head 36b is pivotally coupled to the second arm 36a by a living hinge 36c.

In use, with referenced to FIGS. 1-4B, the knife assembly 30 is actuated through the knife slots 52b, 54b of the first and second jaw members 52, 54 to effectuate a distal cutting of tissue disposed between the first and second jaw members 52, 54. The first head 34b of the knife assembly 30 is positioned to maintain a first cutting height "H1" (see FIG. 4A) of the knife assembly 30 along the first length "L1" (see FIG. 3C) of the first portion 53a of the knife channel 53 of the first and second jaw members 52, 54. As the first head 34b of the knife assembly 30 travels along the second length "L2" (see FIG. 3C) of the second portion 53b of the knife channel 53 of the first and second jaw members 52, 54, the first head 34b of the knife assembly 30 transitions (e.g., pivots) to move the knife assembly 30 toward a second cutting height "H2" (see FIG. 4B) of the knife assembly 30. The second cutting height "H2" of the knife assembly 30 may be smaller than the first cutting height "H1" of the knife assembly 30 to effectuate finer tissue cutting with the knife assembly 30. In some embodiments, the first head 34b of the knife assembly 30 maintains the knife assembly 30 at the second cutting height "H2" while travelling along the third length "L3" (see FIG. 3C) of the third portion 53c of the knife channel 53. To effectuate pivoting movement of the first head 34b of the knife assembly 30 relative to the first arm 34a of the knife assembly 30 (and the second head 36b toward the second arm 36a of the knife assembly 30), the one or more engagement surfaces 34f, 34g of the first head 34b of the first arm 34a are positioned to contact at least a point/surface or portion of the surfaces defining the knife channel 53 of the first and second jaw members 52, 54 (e.g., the second portion 53b of the knife channel 53). For example, engagement with the second portion 53b of the knife channel 53, and distal advancement therealong, may cause the first head 34b of the first arm 34a to pivot the second head 36b of the second arm 36a via the living hinge 36c so that the first head 34b of the first arm 34a pivots beneath the second head 36b of the second arm 36a to receive the second head 36b of the second arm 36a within the notch 34e of the first head 34b.

In some embodiments, the knife slots 52b, 54b, or portions thereof, may include one or more contact surfaces (e.g., at one or more predetermined locations therealong) such as a bump, protuberance and/or surface texturing (not shown). The contact surfaces may apply frictional forces to the first head 34b of the first arm 34a to effectuate rotational/pivoting movement of the first head 34b of the first arm 34a relative to the first arm 34a (and/or relative to the second arm 36a and/or the second head 36b of the second arm 36a) via the living hinge 34c as the knife assembly 30 translates distally through the knife slots 52b, 54b and/or knife channel 53.

As the first and second arms 34a, 36a of the knife assembly 30 and the first and second heads 34b, 36b of the knife assembly 30 approximate toward one another in response to movement from the first cutting height "H1" toward the second cutting height "H2," a first gap height "G1" of the gap 38 defined between the first and second arms 34a, 36a, reduces to a second gap height "G2" so that the first head 34b of the first arm 34a can fold over the second head 36b of the second arm 36a and a cutting height of the knife assembly 30 can be reduced such that the knife blade 34d can be received within the second and/or third portions 53b, 53c of the knife channel 53 for effectuating finer distal dissection with the knife assembly 30 along the tips 52c, 54c of the first and second jaw members 52, 54.

The first and/or second gap heights "G1", "G2" may vary along the length of the first and/or second arms 34a, 36a of the knife assembly 30 with the first gap height "G1" generally being greater than the second gap height "G2" at any given longitudinal location along the length of the first and/or second arms 34a, 36a of the knife assembly 30. In some embodiments, the first gap height "G1" at a proximal end of the first and/or second arms 34a, 36a of the knife assembly 30 may be larger than the first gap height "G1" at a distal end of the first and/or second arms 34a, 36a of the knife assembly 30. Likewise, in some embodiments, the second gap height "G2" at a proximal end of the first and/or second arms 34a, 36a of the knife assembly 30 may be larger than the second gap height "G1" at a distal end of the first and/or second arms 34a, 36a of the knife assembly 30.

Turning now to FIGS. 5A-5D, another embodiment of a knife assembly of the present disclosure, generally referred to as knife assembly 100, is provided. Knife assembly 100 defines a longitudinal axis "X2" between proximal and distal ends of the knife assembly 100 and includes a knife body 102 having a first arm 104a and a second arm 106a positioned in vertical registration with one another. The first and second arms 104a, 106a extend distally from the knife body 102 and are spaced apart by a gap 108 defined between inner surfaces of the first and second arms 104a, 106a. The knife body 102 may support a stop ramp 110 or the like to limit distal axial translation of the knife assembly 100 through the knife channel 53. For example, the stop ramp 110 can be utilized to limit the risk of blade dulling (e.g. of knife blade 104d) against distal surfaces that define the knife slots 52b, 54b of first and second jaw members 52, 54 (see FIGS. 3A and 3B).

The first arm 104a of the knife assembly 100 extends distally to a first head 104b pivotally coupled to the first arm 104a by a living hinge 104c. A distal surface of the first head 104b supports a knife blade 104d and a proximal surface of the first head 104b defines a notch 104e therein. The first head 104b and the knife blade 104d are curved. The first arm 104a further defines a first ramp 104f between a pair of offset surfaces 104g, 104h disposed in different planes relative to the longitudinal axis "X2."

The second arm 106a of the knife assembly 100 extends distally to a second head 106b selectively receivable within the notch 104e of the first head 104b of the first arm 104a. The second head 106b of the second arm 106a may have any suitable configuration, such as rounded or blunt. The second head 106b is pivotally coupled to the second arm 106a by a living hinge 106c. The second arm 106a further includes a second ramp 106d between a pair of offset surfaces 106e, 106f disposed in different planes relative to the longitudinal axis "X2." The first and second ramps 104f, 106d of the first and second arms 104a, 106a, respectively, may be longitudinally offset relative to the longitudinal axis "X2."

In use, the knife assembly 100 is advanced distally through the knife slots 52b, 54b and the bifurcated pivot boss 60 of first and second jaw members 52, 54 such that the second head 106b of the second arm 106a supports the first head 104b of the first arm 104a to maintain the knife blade 104d of the first head 104b in position so that the knife assembly 100 is disposed at the first cutting height "H1" similar to that described above with respect to knife assembly 30.

To reduce the cutting height of the knife assembly 100 from the first cutting height "H1" to the second cutting height "H2," the first and second ramps 104f, 106d of the first and second arms 104a, 106a successively engage surfaces of the bifurcated pivot boss 60 as the knife assembly 100 distally translates through the first and second jaw members 52, 54. As the first and second ramps 104f, 106d of the first and second arms 104a, 106a engage the bifurcated pivot boss 60, the first head 104d of the first arm 104a folds around and under the second head 106b of the second arm 106a to receive the second head 106b within the notch 104e of the first head 104b. The second ramp 106d of the second arm 106a engages a proximal surface of the second opposing half 60b of the bifurcated pivot boss 60 and the first ramp 104f of the first arm 104a engages a proximal surface of the first opposing half 60a of the bifurcated pivot boss 60. While the first and second ramps 104f, 106d of the respective first and second arms 104a, 106a can be arranged in any suitable longitudinal offset position relative to one another along the longitudinal axis "X2," in some embodiments, the first and second ramps 104f, 106d can be arranged in longitudinal alignment with one another along the longitudinal axis "X2."

Referring now to FIGS. 6-9C, another embodiment of a knife assembly of the present disclosure, referred to generally as knife assembly 200, is provided. The knife assembly 200 defines a longitudinal axis "X3" between proximal and distal ends thereof and includes a knife body 202 having a first arm 204a and a second arm 206a positioned in vertical registration with one another. The first and second arms 204a, 206a extend distally from the knife body 202 and are spaced apart by a gap 208 defined between inner surfaces of the first and second arms 204a, 206a. The knife body 202 may support a stop ramp 210 (FIG. 9A) to limit distal axial translation of the knife assembly 200 similar to the stop ramp 110 of the knife assembly 100 described above.

The first arm 204a of the knife assembly 200 extends distally to a first head 204b. A neck 204c, which extends laterally and transverse to the longitudinal axis "X3," couples the first head 204b to the first arm 204a and positions the first head 204b in parallel relation with the longitudinal axis "X3." A living hinge 204d pivotally couples the first head 204b to the first arm 204a via the neck 204c. A distal surface of the first head 204b supports a first knife blade 204e having a longitudinal cutting edge 204f and a transverse cutting edge 204g that intersect at a corner 204h to form a continuous cutting surface. The first arm 204a further defines a first ramp 204i between a pair of offset surfaces 204j, 204k disposed in different planes relative to the longitudinal axis "X3.".

The second arm 206a of the knife assembly 200 extends distally to a second head 206b. A neck 206c of the knife assembly 200, which extends laterally and transverse to the longitudinal axis "X3," couples the second head 206b to the second arm 206a and positions the second head 206b in parallel relation with the longitudinal axis "X3" and relative to the first head 204b of the first arm 204a. A distal surface of the second head 206b supports a second knife blade 206d having a longitudinal cutting edge 206e and a transverse cutting edge 206f that intersect at a corner 206g to form a continuous cutting surface.

The first and second heads 204b, 206b of the first and second arms 204a, 206a, respectively, are arranged so that the cutting edges thereof are positioned to create a scissor-cutting action. The continuous cutting surfaces of the first and second heads 204b, 206b of the first and second arms 204a, 206a may be disposed in mirrored relation to facilitate the scissor-cutting action.

In use, the knife assembly 200 is advanced distally through the bifurcated pivot boss 60 and knife channel 53 of first and second jaw members 52, 54. After distally advancing that knife assembly 200 along a predetermined length through the first and second jaw members 52, 54, the ramp 204i of the first arm 204a contacts the bifurcated pivot boss 60 (e.g., the first opposing half 60a) to effectuate pivoting movement of the first head 204b of first arm 204a toward the second head 206b of the second arm 206a and a reduction in a cutting height of the knife assembly 200 from the first cutting height "H1" to the second cutting height "H2." The cutting height of the knife assembly 200 is defined by the first and second knife blades 204e, 206d of the first and second heads 204b, 206b. The first and second knife blades 204e, 206d are configured to cut in shear and/or axial directions relative to the longitudinal axis "X3" of the knife assembly 200 as the knife assembly 200 transitions (e.g., scissor-cutting action) from the first cutting height "H1" to the second cutting height "H2." Once the knife assembly 200 is positioned at the second cutting height "H2," the first and second knife blades 204e, 206d are configured to cut solely in an axial direction upon further distal advancement of the knife assembly 200 through the first and second jaw members 52, 54.

Turning now to FIGS. 10A-10D, yet another embodiment of a knife assembly of the present disclosure, referred to generally as knife assembly 300, is provided. The knife assembly 300 defines a longitudinal axis "X4" between the proximal and distal ends thereof and includes a knife body 302 having a first arm 304a, and a second arm 306a positioned in vertical registration with one another. The first and second arms 304a, 306a of the knife assembly 300 extend distally from the knife body 302 and are spaced apart by a gap 308 defined by inner surfaces of the first and second arms 304a, 306a. The knife body 302 may support a stop ramp 310 to limit distal axial translation of the knife assembly 300 similar to the stop ramp 110 of the knife assembly 100 described above.

The first arm 304a of the knife assembly 300 extends distally to a first head 304b pivotally coupled to the first arm 304a by a living hinge 304c. A distal surface of the first head 304b of the knife assembly 300 supports a knife blade 304d and a proximal surface of the first head 104b defines a notch 304e therein. The knife blade 304d may include a pair of cutting edges 304f, 304g, transverse to one another, which intersect at a corner 304h of the first head 304b of the first arm 304a. The first head 304b of the first arm 304a further includes a first engagement surface 304i disposed adjacent to the knife blade 304d. The first engagement surface 304i of first head 304b of the knife assembly 300 is configured to contact a first engagement surface 52e defined by the first jaw member 52 within the knife slot 52b of the first jaw member 52 to impart pivotal movement of the first head 304b of the knife assembly 300 relative to the first arm 304a of the knife assembly 300.

The second arm 306a of the knife assembly 300 extends distally to a second head 306b selectively receivable within the notch 304e of the first head 304b. The second head 306b is pivotally coupled to the second arm 306a by a living hinge 306c. The second head 306b of the second arm 306a further includes a second engagement surface 306d disposed adjacent to the living hinge 306c. The second engagement surface 306d of the second head 306b of the knife assembly 300 is configured to contact a second engagement surface 54e defined by the second jaw member 54 within the knife channel 54b of the second jaw member 54 to impart pivotal movement of the second head 306b of knife assembly 300 relative to the second arm 306a of the knife assembly 300.

In use, the knife assembly 300 is advanced distally through the knife slots 52b, 54b and the bifurcated pivot boss 60 of first and second jaw members 52, 54 such that the second head 306b of the second arm 306a of the knife assembly 300 supports the first head 304b of the first arm 304a to maintain the knife assembly 300 at the first cutting height "H1" similar to that described above with respect to the knife assembly 30.

To reduce the cutting height of the knife assembly 300 to the second cutting height "H2," the first and second ramps 304i, 306d of the first and second heads 304b, 306b of the first and second arms 304a, 306a successively engage the engagement surfaces 52e, 54e of the first and second jaw members 52, 54, respectively, as the knife assembly 300 distally translates through the knife channel 53 of the first and second jaw members 52, 54.

The first and second heads 304b, 306b of the knife assembly 300 are positioned so that the first head 304b of the first arm 304a folds around and under the second head 306b of the second arm 306a to receive the second head 306b within the notch 304e of the first head 304b similar to that described above with respect to the knife assembly 100. The engagement surfaces 52e, 54e of the first and second jaw members 52, 54 can be arranged in any suitable longitudinal offset position relative to one another to facilitate the above described approximating/pivoting movement of the first and second heads 304b, 306b. In some embodiments, the engagement surfaces 52e, 54e of the respective first and second jaw members 52, 54 can be arranged in longitudinal alignment with one another.

Any of the presently described knife assemblies, or components thereof (e.g., living hinges) may be flexibly and/or resiliently biased toward the first and/or second cutting heights "H1," "H2." In some embodiments, one or more of the presently described living hinges may be replaced with any suitable hinge such as a pinned hinge or the like (not shown).

Any of the presently described surfaces may be defined by single or multiple points. In some embodiments, one or more of the presently described surfaces may include one or more ramps, inclines, etc.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 11:
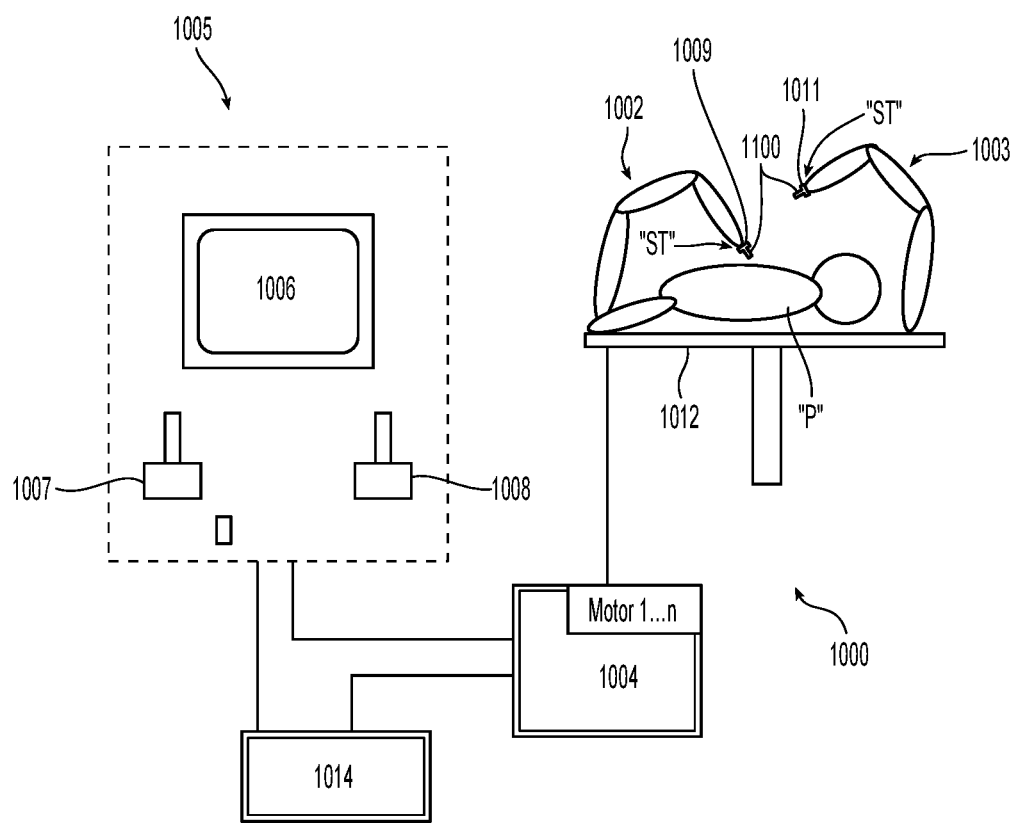
FIG. 11 is a schematic illustration of a medical work station and operating console in accordance with the present disclosure.

Referring also to FIG. 11, a medical work station is shown generally as work station 1000 and generally may include a plurality of robot arms 1002, 1003; a control device 1004; and an operating console 1005 coupled with the control device 1004. The operating console 1005 may include a display device 1006, which may be set up in particular to display three-dimensional images; and manual input devices 1007, 1008, by means of which a person (not shown), for example a clinician, may be able to telemanipulate the robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1100 (e.g., a pair of jaw members), in accordance with any one of several embodiments disclosed herein, as will be described in greater detail below.

The robot arms 1002, 1003 may be driven by electric drives (not shown) that are connected to the control device 1004. The control device 1004 (e.g., a computer) may be set up to activate the drives, in particular by means of a computer program, in such a way that the robot arms 1002, 1003, their attaching devices 1009, 1011 and thus the surgical tool (including the end effector 1100) execute a desired movement according to a movement defined by means of the manual input devices 1007, 1008. The control device 1004 may also be set up in such a way that it regulates the movement of the robot arms 1002, 1003 and/or of the drives.

The medical work station 1000 may be configured for use on a patient "P" lying on a patient table 1012 to be treated in a minimally invasive manner by means of the end effector 1100. The medical work station 1000 may also include more than two robot arms 1002, 1003, the additional robot arms likewise connected to the control device 1004 and telemanipulatable by means of the operating console 1005. A medical instrument or surgical tool (including an end effector 1100) may also be attached to the additional robot arm. The medical work station 1000 may include a database 1014 coupled with the control device 1004. In some embodiments, pre-operative data from patient/living being "P" and/or anatomical atlases may be stored in the database 1014.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

The invention claimed is:

1. A knife assembly of a surgical end effector assembly, the knife assembly comprising:
a knife body defining a longitudinal axis and having first and second arms, the first arm having a first head including a cutting edge at a distal end thereof and the second arm having a second head, the first head including a notch defined in a proximal end thereof, the notch configured to receive the second head therein, wherein at least the first head is pivotable relative to the second head to reduce a cutting height during translation of the knife assembly through a knife channel defined within the end effector assembly.

2. The knife assembly of claim 1, wherein the first arm defines a first ramp configured to move the first arm relative to the second arm during translation of the knife assembly through the knife channel.

3. The knife assembly of claim 2, wherein the second arm defines a second ramp configured to move the second arm relative to the first arm during translation of the knife assembly through the knife channel.

4. The knife assembly of claim 3, wherein the first and second ramps are longitudinally offset from one another.

5. The knife assembly of claim 1, wherein the first head is configured to matingly receive the second head while the second head is received within the notch of the first head.

6. The knife assembly of claim 1, wherein relative pivoting movement between the first and second heads causes the first and second heads to move between an unapproximated position and an approximated position, the first and second arms remaining in the same plane while the first and second heads are in both the unapproximated and approximated positions.

7. The knife assembly of claim 1, wherein the first head defines a first head ramp configured to pivot the first head relative to the first arm and the second head defines a second head ramp configured to pivot the second head relative to the second arm, the first and second heads pivotable during translation of the knife assembly through the knife channel.

8. The knife assembly of claim 7, wherein the first and second head ramps are longitudinally offset.

9. The knife assembly of claim 1, wherein the first head is pivotally coupled to the first arm by a living hinge.

10. The knife assembly of claim 1, wherein the second head includes a cutting edge, the cutting edges of the first and second heads positioned to create a scissor-cutting action between the cutting edges thereof as at least the first head pivots relative to the second head.

11. The knife assembly of claim 10, wherein the cutting edge of the first head includes a first longitudinal cutting edge and a first transverse cutting edge, the cutting edge of the second head includes a second longitudinal cutting edge and a second transverse edge, the first and second longitudinal cutting edges configured to cut in a shear direction transverse to the longitudinal axis of the knife body, the first and second transverse cutting edges configured to cut in an axial direction along the longitudinal axis of the knife body.

12. The knife assembly of claim 11, wherein the first longitudinal cutting edge is joined with the first transverse cutting edge by a first corner and the second longitudinal cutting edge is joined to the second transverse cutting edge by a second corner, the first and second corners configured to cut in both the shear and axial directions relative to the longitudinal axis of the knife body.

13. The knife assembly of claim 1, wherein the first head is coupled to the first arm by a first neck, the first neck extending transverse to the longitudinal axis of the knife body.

14. A knife assembly of a surgical end effector assembly, the knife assembly comprising:
- a knife body defining a longitudinal axis and having first and second arms, the first arm having a first head including a cutting edge at a distal end thereof and the second arm having a second head, the second head including a cutting edge, the cutting edges of the first and second heads positioned to create a scissor-cutting action between the cutting edges thereof as at least the first head pivots relative to the second head,
- wherein the cutting edge of the first head includes a first longitudinal cutting edge and a first transverse cutting edge, the cutting edge of the second head includes a second longitudinal cutting edge and a second transverse edge, the first and second longitudinal cutting edges configured to cut in a shear direction transverse to the longitudinal axis of the knife body, the first and second transverse cutting edges configured to cut in an axial direction along the longitudinal axis of the knife body, and
- wherein at least the first head is pivotable relative to the second head to reduce a cutting height during translation of the knife assembly through a knife channel defined within the end effector assembly.

15. The knife assembly of claim 14, wherein the first longitudinal cutting edge is joined with the first transverse cutting edge by a first corner and the second longitudinal cutting edge is joined to the second transverse cutting edge by a second corner, the first and second corners configured to cut in both the shear and axial directions relative to the longitudinal axis of the knife body.

* * * * *